(12) United States Patent  (10) Patent No.: US 7,698,905 B1
Carpenter et al.  (45) Date of Patent: Apr. 20, 2010

(54) COOLING DEVICE

(75) Inventors: William K. Carpenter, Warrensville, NC (US); Gregory S. Patterson, Morrisville, NC (US); Sean M. Ahr, Morrisville, NC (US); Jonathan Deline, Oak Ridge, NC (US); Debbie Deline, Oak Ridge, NC (US)

(73) Assignee: Porticool, Inc., Morrisville, NC (US)

( * ) Notice: Subject to any disclaimer, the term of this patent is extended or adjusted under 35 U.S.C. 154(b) by 0 days.

(21) Appl. No.: 12/146,084

(22) Filed: Jun. 25, 2008

Related U.S. Application Data

(62) Division of application No. 11/142,637, filed on Jun. 1, 2005, now Pat. No. 7,527,612.

(60) Provisional application No. 60/587,756, filed on Jul. 14, 2004.

(51) Int. Cl.
*F25D 23/12* (2006.01)
(52) U.S. Cl. .................................................. 62/259.3
(58) Field of Classification Search ................ 62/259.3, 62/384, 388; 604/291–293
See application file for complete search history.

(56) References Cited

U.S. PATENT DOCUMENTS

| | | | |
|---|---|---|---|
| 3,049,896 A | 8/1962 | Webb | |
| 4,738,119 A | 4/1988 | Zafred | |
| 5,438,707 A | 8/1995 | Horn | |
| 6,209,144 B1 | 4/2001 | Carter | |
| 6,295,648 B2 | 10/2001 | Siman-Tov et al. | |
| 6,584,798 B2 | 7/2003 | Schegerin | |
| 6,681,589 B2 | 1/2004 | Brudnicki | |

FOREIGN PATENT DOCUMENTS

GB 1376604 A 12/1974

*Primary Examiner*—Melvin Jones
(74) *Attorney, Agent, or Firm*—Coats & Bennett, P.L.L.C.

(57) ABSTRACT

A cooling garment including an inlet for receiving a cooling medium such as $CO_2$. A series of conduits are associated with the garment. In a first cooling stage, the cooling medium or $CO_2$ passes through the one or more conduits and undergoes a phase change where the cooling medium or $CO_2$ changes from a predominantly liquid phase to a predominantly gaseous phase. In this first stage, heat is transferred from a living body having the garment disposed adjacent thereto the cooling medium or $CO_2$. In a second stage of cooling, the cooling medium or $CO_2$ assumes a substantial gaseous phase and the gaseous cooling medium or $CO_2$ is dispersed onto the garment or the body resulting in the body being cooled through evaporative cooling.

20 Claims, 4 Drawing Sheets ized Self-Contained Systems
COOLING DEVICE

CROSS REFERENCE TO RELATED APPLICATION

The present application is a divisional of U.S. patent application Ser. No. 11/142,637 filed Jun. 1, 2005 entitled "A Cooling Device;" which claims priority under 35 U.S.C. §119 (e) from U.S. provisional patent application: Application Ser. No. 60/587,756 filed on Jul. 14, 2004. These applications are incorporated in their entirety by reference herein.

FIELD OF THE INVENTION

The present invention relates to providing effective personal cooling for individuals wearing Personal Protective Equipment (PPE).

BACKGROUND OF THE INVENTION

Personnel working in hazardous environments are advised and often required by regulations to wear Personal Protective Equipment (PPE) to protect them from the negative and injurious effects of the environment in which their activities take place. Among the kinds of situations in which PPE is in order are Emergency Response, Hazardous Materials Handling, and Severe Environmental Conditions.

PPE generally consists of respiratory protection and percutaneous protection. Respiratory protection consists of a variety of masks and filtration systems and/or sources of breathable air. Percutaneous protection consists of garments configured to prevent contact of harmful agents with the skin. When combined, the resulting PPE renders the individual protected more or less sealed in a garment. While such garments typically have check valves to vent gases built up within the garment interior, the check valves do not admit any materials into the suit from the surrounding environment.

In order to provide for the comfort and safety of personnel using PPE, means must be provided for maintaining a habitable thermal environment within the PPE. Failure to do so results in buildup of heat and a resulting uncomfortable—at least, and more often deleterious—heat stress for the individual protected by the PPE.

Various technologies exist or have been investigated to cool portions of the garments worn by the personnel to counter or delay the onset of heat stress. These include phase change vests using Phase Change Materials (PCM), Tethered Systems (TS), and Miniaturized Self-Contained Systems (MSCS) to absorb heat from the body torso. PCM materials such as paraffin, hydrated salts, and ice may be packed or juxtaposed with appropriate garment portions, and these "frozen materials" absorb sensible heat from the body by melting. TS comprise some kind of external refrigeration system to which the personnel is "tethered" by supply lines providing the cooling. MSCS use vapor-compression, thermoelectric, magnetocaloric, pulse-tube, thermionic, and thermoacoustic principles, among others, to provide on board cooling. Field tests of PCM-based systems have not shown them to be effective. Further, there is the need to refreeze the PCM or replace it. While TS are generally quite effective in providing cooling, they severely limit the mobility of the individual being protected, thus limiting the individual's effectiveness and responsiveness in emergency situations. Existing MSCS systems generally rely on battery devices which add weight and generate additional heat load. No technologies in use effectively deal with removal of perspiration, and many do not effectively dissipate heat away from the body.

An effective and efficient PPE cooling system is needed which will provide maximum flexibility and freedom of movement for the wearer. Personnel involved in rescue and other first responder activities are among those who will benefit from such a system.

SUMMARY OF THE INVENTION

The present invention relates to a cooling device that comprises a garment and one or more conduits for distributing a cooling medium to one or more areas of the garment such that the garment is effective to cool the wearer of the garment. In one embodiment, a source of carbon dioxide ($CO_2$) that is operatively connected to the one or more conduits for directing the carbon dioxide through the conduits. Heat from the wearer is transferred to the $CO_2$.

In another embodiment of the present invention, the cooling device includes a garment, a cooling medium inlet, one or more conduits associated with the garment to hold the cooling medium, and a control for controlling the phase of the cooling medium such that two-stage cooling is achieved. In a first stage at least a portion of the cooling medium assumes a liquid state and in a second stage, the cooling medium assumes a gaseous state. Heat from the living body is transferred to the cooling medium as it moves through the conduits in the first stage. Further, in the second stage, the conduits are arranged to disperse the gaseous cooling medium and cool the living body through evaporative cooling.

In addition, the present invention entails a method of cooling a living body or a part thereof within a garment. The method entails directing $CO_2$ to the garment and distributing the $CO_2$ about one or more areas of the garment. Heat is transferred from the living body or a part thereof to the $CO_2$.

The present invention also entails a method of cooling a living body with a biphasic cooling medium. In this method, the cooling medium assumes a substantial gaseous phase and the gaseous cooling medium is dispersed onto the body or to an area adjacent the body so as to effectuate evaporative cooling of the living body.

Other objects and advantages of the present invention will become apparent and obvious from a study of the following description and the accompanying drawings which are merely illustrative of such invention.

DESCRIPTION OF EXEMPLARY EMBODIMENT

Figure 1:
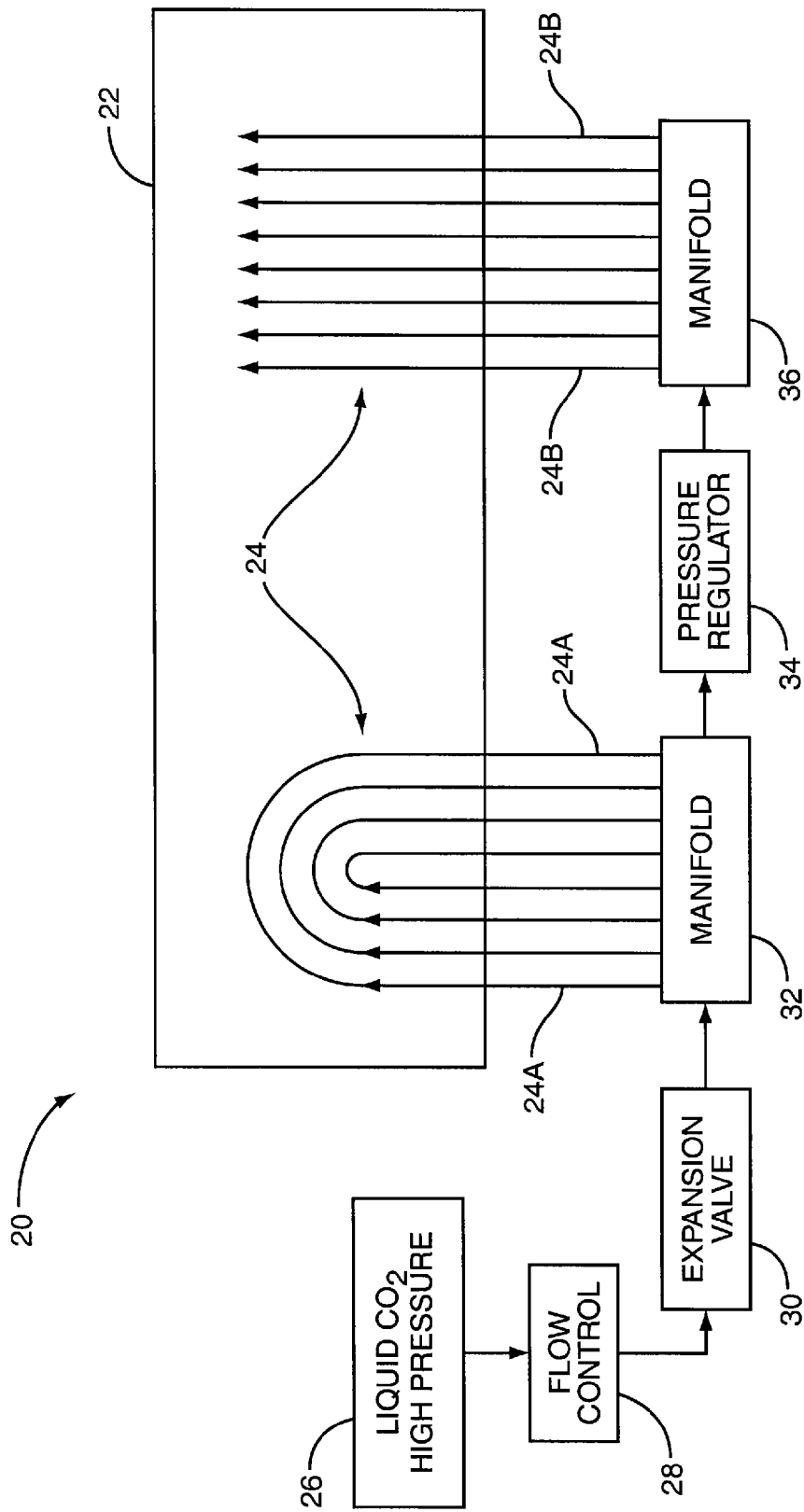
FIG. 1 is a schematic illustration of the cooling system of the present invention.
Figure 2:
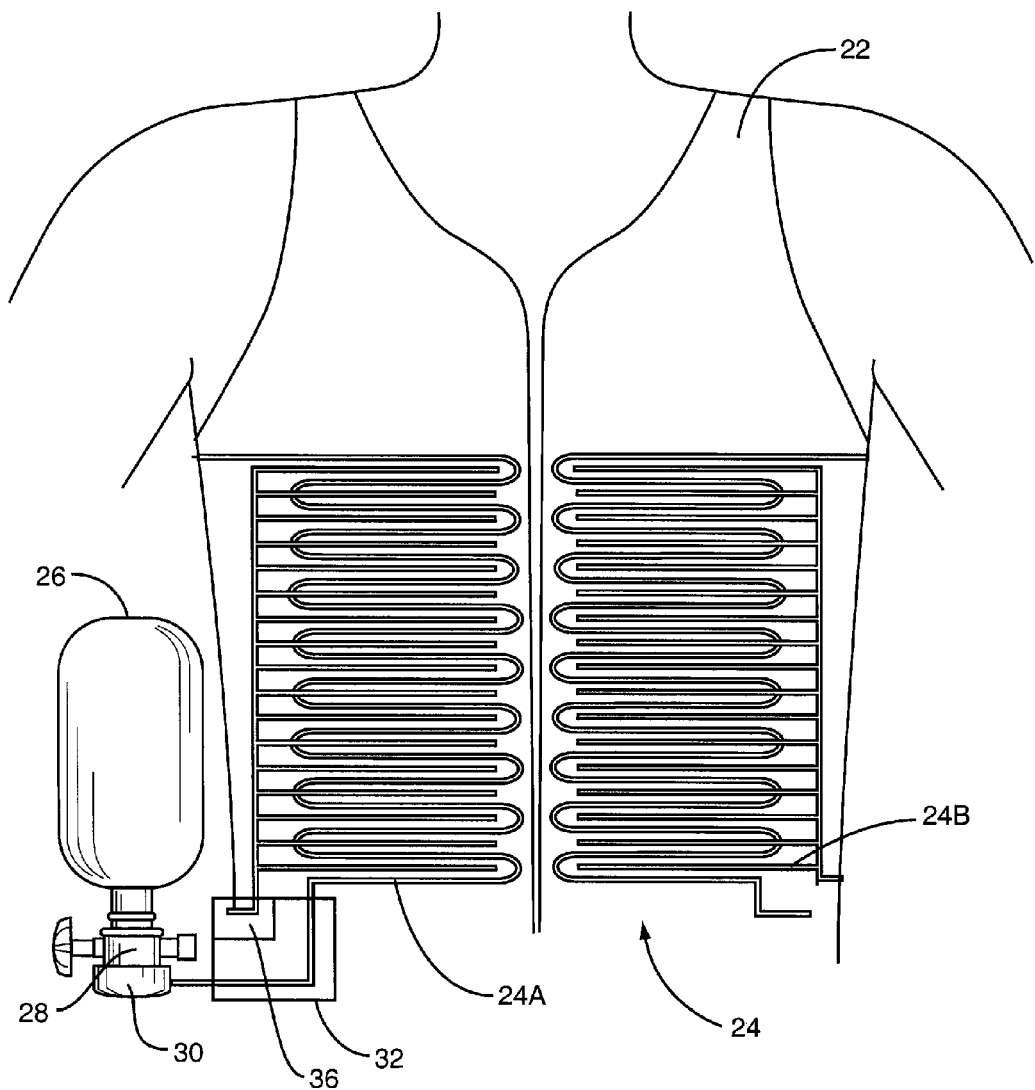
FIG. 2 is a schematic illustration of the cooling system and shows various components thereof.
Figure 3:
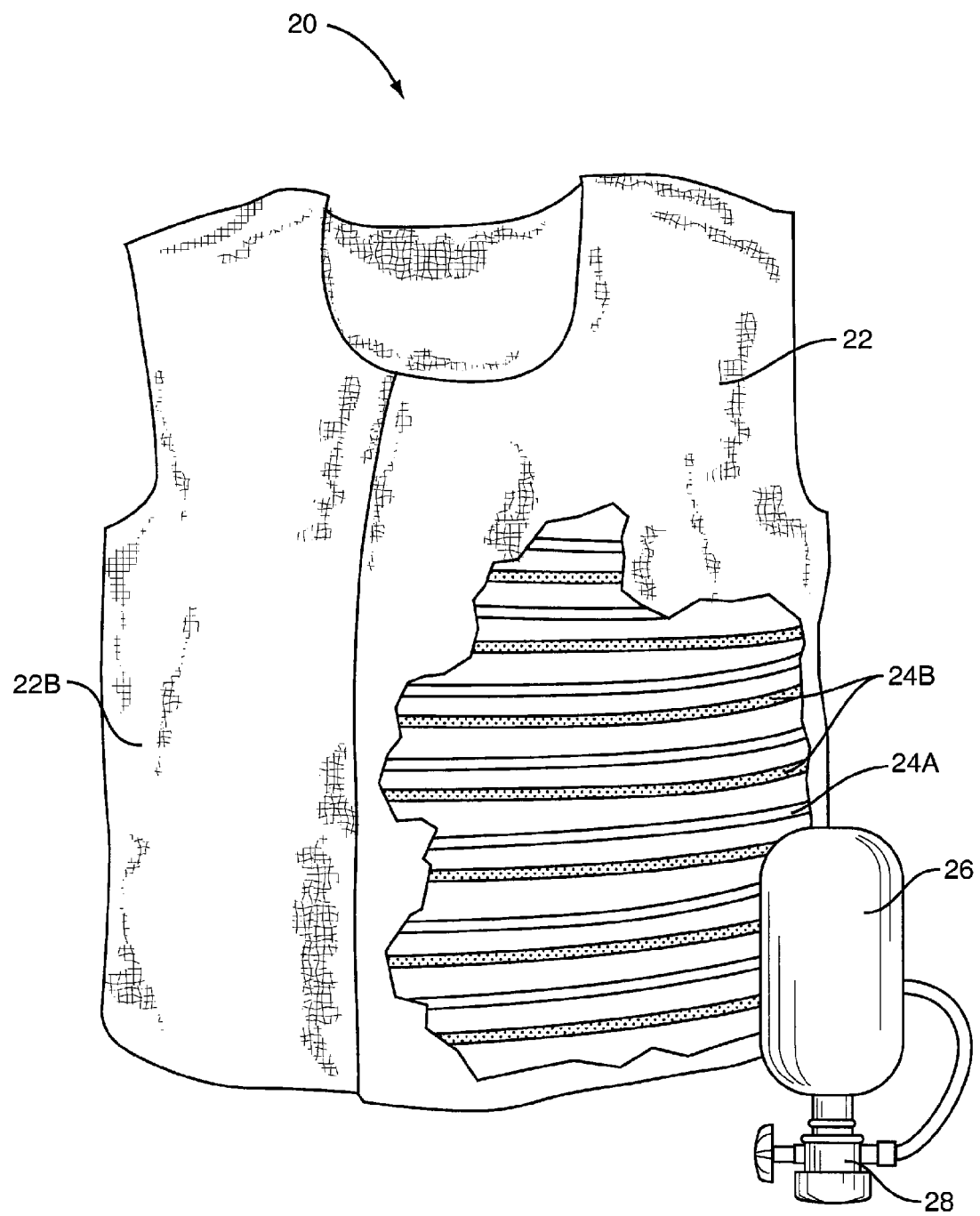
FIG. 3 illustrates various components of the cooling system including a garment and a canister for holding a cooling media.
Figure 4:
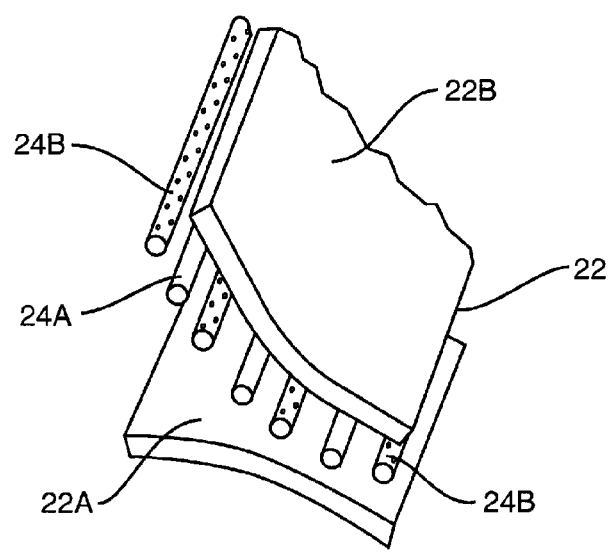
FIG. 4 is a small schematic view illustrating a portion of the garment and the conduits extending therein.
Figure 5:
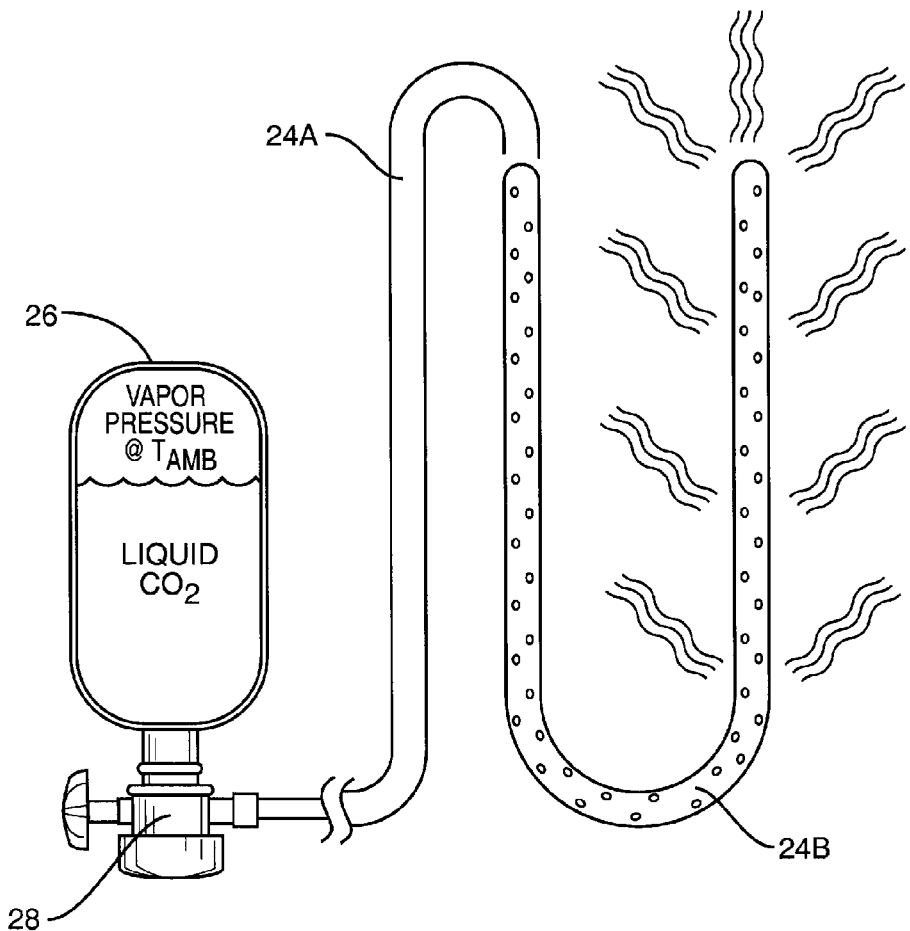
FIG. 5 is a schematic illustration of the cooling system of the present invention and which illustrates the two-stage cooling principle.

With further reference to the drawings, the cooling device of the present invention is shown therein and indicated generally by the numeral 20. Cooling device 20 is designed to be worn or used by a living body to cool the living body. As will be appreciated from subsequent portions of the disclosure, cooling device 20 utilizes a cooling medium such as carbon dioxide ($CO_2$). The cooling medium is directed in close proximity to the living body such that heat from the living body is transferred during a first cooling stage to the cooling medium. In a second cooling stage, the cooling medium assumes a substantially gaseous phase and is dispersed in close proximity to the body to effectuate evaporative cooling of the body.

Turning to the cooling device 20, the same comprises a garment 22. Garment 22 is adapted to be worn or disposed adjacent a living body. The term garment, as used herein, encompasses worn objects or an object or device that when used is placed in close proximity to a living body such that heat can be transferred between the object or device and a living body. Associated with the garment is one or more conduits. As will be appreciated from subsequent portions of the disclosure, the one or more conduits is generally referred to by the numeral 24 and in one embodiment includes a first set of conduits 24A and a second set of conduits 24B. The conduits that make up the first and second sets 24A and 24B include elongated plastic tubes that are effective to convey the cooling medium. The first set of conduits 24A includes a closed wall structure that permits the cooling medium to be conveyed from an inlet end portion to an outlet end portion. The conduits that make up the second set 24B are provided with a multiplicity of openings 40 formed in the wall structure thereof that permits the cooling medium to be dispersed therefrom.

As noted above, cooling device 20 utilizes a cooling medium to cool a living body. Hence cooling device 20 includes a cooling medium inlet. When the cooling device 20 is used, a cooling medium source 26 is secured or operatively associated with the device so as to direct a cooling medium into the cooling medium inlet of the cooling device. In the case of one embodiment, the cooling medium source is $CO_2$. The $CO_2$ is housed under pressure within a canister. When in the canister the $CO_2$ assumes a liquid phase or at least a substantial liquid phase. Forming a part of the canister, or located just downstream from the canister or cooling source 26, is a flow control valve 28. Flow control valve 28 functions as a shut off valve that permits the flow of the cooling medium into the conduits 24 to be controlled. By adjusting the flow control valve 28, the cooling rate or cooling capacity of the cooling device 20 can be adjusted.

Disposed adjacent the flow control valve 28 and downstream therefrom is an expansion device 30. Expansion device 30 functions to convert a portion of the cooling medium from a liquid phase to a gas phase. Details of the expansion device 30 are not dealt with herein because such is not per se material to the present invention and further, expansion devices are well known in the art. Suffice to say that the expansion device 30 is preferably insulated and in one particular embodiment would include a coiled tubing that would permit a portion of the liquid cooling medium to expand into a gas adiabatically. As will be discussed subsequently herein, the expansion device 30 in one embodiment is designed to convert the cooling medium from a state where substantially all of the cooling medium assumes a liquid form to a biphasic state where the cooling medium is predominantly in the form of a liquid, but includes a significant gaseous portion. In this embodiment, initially the cooling medium is held within the canister and under substantial pressure and assumes a 100% or near 100% liquid phase. After the cooling medium has passed through the expansion device the cooling medium would assume by weight, for example, a 75% liquid phase and a 25% gas phase.

As illustrated in FIG. 1, disposed between the first set of conduits 24A and the expansion device 30 is a manifold 32. Manifold 32 functions to direct the cooling medium exiting the expansion device 30 into a series of conduits that make up the first set of conduits 24A. Further, disposed downstream of manifold 32 is a backpressure regulator 34. Backpressure regulator 34 is operative to adjust and maintain the pressure of the cooling medium within a staged range in the first set of conduits 24A. Functionally, the cooling medium undergoes phase changes as it moves through the cooling device 20. Expansion device 30 and the backpressure regulator 34 form a control for managing the phase changes of the cooling medium as the cooling medium moves through the cooling device 20. The expansion device 30, in combination with the backpressure regulator 34, play a role in adjusting the pressure of the cooling medium, especially in the first set of conduits 24A.

Disposed downstream of the backpressure regulator 34 is a second manifold 36. Second manifold 36 is communicatively connected to the individual conduits that make up the second set of conduits 24B. Thus, as illustrated in FIG. 1, after exiting the expansion device 30, the cooling medium flows into manifold 32 which disperses the cooling medium into the respective conduits making up the first set of conduits 24A. The first set of conduits 24A are arranged with respect to the manifold 32 such that the cooling medium is directed back to manifold 32 and onto pressure regulator 34 and then onto the second manifold 36 where the cooling medium is directed into the inlet ends of the respective conduits making up the second set of conduits 24B.

Referring to the garment 22, the embodiment shown in the drawings comprises a vest designed or adapted to surround a portion of the torso of a human being. It is appreciated that the garment 22 can assume various forms. The term garment, as used herein, encompasses material that is used to support one or more conduits 24 in close proximity to a living body for the purpose of extracting heat for cooling the living body. Garment 22 can be utilized to cool living bodies other than human beings'. In the embodiment illustrated herein the garment, as noted above, comprises a vest-type garment that includes first and second layers 22A and 22B. First layer 22A is designed to lay adjacent the living body and could be constructed of a hyperphilic material or fabric. The other layer 22B would ordinarily be disposed outwardly of the first layer 22A and could be constructed of a hydrophobic material or fabric. In this particular embodiment, conduits 24 are uniformly wound and distributed about the garment or a selected area of the garment 22. The respective conduits would be secured such that they extend generally between the first and second layers 22A and 22B. These conduits could extend in channels formed by stitch patterns that extended between the first and second layers 22A and 22B of the garment 22. Because the two sets of conduits perform two different types of cooling, each set of conduits would be wound and distributed about the same area. Thus, one or more conduits of the first set 24A would extend alongside one or more conduits of the second set 24B.

Although other biphasic cooling mediums may be used, it is contemplated that $CO_2$ would form a practical and cost effective cooling medium for use in conjunction with the cooling device 20. $CO_2$ would be containerized or housed within a canister at a selected pressure such as 800 psi. At 800 psi $CO_2$ assumes a liquid or near liquid phase. By opening the flow control valve 28 downstream from the canister, the $CO_2$ within the canister is permitted to flow through the expansion device 30. While various pressure drops can be achieved, it is contemplated that in one design the pressure of the $CO_2$ exiting the expansion device 30 would be approximately 300 psi. In moving through the expansion device 30, the $CO_2$ adiabatically expands and assumes a biphasic state where approximately 75% (by weight) of the $CO_2$ assumes a liquid phase and approximately 25% (by weight) of the $CO_2$ assumes a gaseous phase. These percentages can vary. However, in one embodiment it is contemplated that $CO_2$ leaving the expansion device would be predominantly in a liquid form or phase, but yet a significant portion of the $CO_2$ would assume a gaseous phase.

From the expansion device 30, the biphasic $CO_2$ enters the first manifold 36 and from the manifold 32 the biphasic $CO_2$ is directed through the individual conduits that make up the first set of conduits 24A. As the $CO_2$ moves through the first set of conduits 24A, heat is conducted from the wearer to the $CO_2$. The heat from the wearer supplies the latent heat of evaporation that causes the liquid portion of the biphasic $CO_2$ to progressively evaporate to the gaseous state as the $CO_2$ moves through the first set of conduits 24A. This cools the living body disposed next to the garment 22. This particular cooling process is referred to as a first stage cooling process. Flow rate and conduit diameter and length are selected so that in a typical application the liquid $CO_2$ is substantially evaporated in the first stage. Thus, all, or substantially all, of the $CO_2$ entering the second set of conduits 24B assume a gaseous and dry state.

The gaseous and dry $CO_2$ flows into the second manifold 36 at atmospheric pressure and into the second set of conduits 24B. Because the second set of conduits is vented to the atmosphere by openings 40 formed in the walls thereof, the gaseous $CO_2$ is dispersed from the conduits. Depending upon the orientation of the conduits with respect to the garment 22, the gaseous $CO_2$ can be dispersed directly on the living body, onto a portion of the garment 22, or onto both the garment and the living body. In one case, where the conduits 24 are disposed between the first and second layers 22A and 22B, the $CO_2$ is dispersed onto the inner or first layer 22A. Because of the absorbent nature of this inner layer 22A, this layer of the garment absorbs perspiration of the wearer, and the dry $CO_2$ gas promotes evaporation of the moisture accompanied by the absorption of the latent heat of evaporation of the moisture. This further cools the living body. The moist $CO_2$ is vented to the atmosphere. This stage of cooling is referred to as the second stage and basically entails evaporative cooling.

In an application in which the device and the living body are fully enclosed within an outer protective garment, it is appreciated that the $CO_2$ vented from the device will buildup within the outer garment. In such an arrangement, however, provision is made for removing the $CO_2$ from within the outer garment by means of further venting the $CO_2$ to the environment outside the outer garment by means of openings in the outer garment. These openings employ check valves which permit flow only in the direction from within the outer garment to the outside environment. This arrangement effectively ejects the heat from the interior of the outer garment by mass transfer of the $CO_2$.

The particular design of the cooling device 20 can vary. Various cooling mediums can be utilized and the design of the garment 22, conduits 24 and the various controls can vary. In one embodiment it is contemplated that the cooling medium would comprise $CO_2$. A canister containing two pounds of $CO_2$ at 800 psi would provide a significant cooling capacity. In one design, the diameter of the first set of conduits would be approximately 1/32" and the total length of all of the conduits comprising the first set of conduits 24A would be approximately 40'. Likewise, the diameter of the second set of conduits 24B would be approximately 1/32" and their total length would be approximately 20'. The rate of cooling and the cooling capacity can be varied by modifying or changing the structure and components of the cooling device. Furthermore, the rate of cooling can be adjusted on an ongoing basis by turning the flow control valve 28 on and off, or by varying the flow rate of the cooling medium leaving the canister.

The present invention may, of course, be carried out in other specific ways than those herein set forth without departing from the scope and the essential characteristics of the invention. The present embodiments are therefore to be construed in all aspects as illustrative and not restrictive and all changes coming within the meaning and equivalency range of the appended claims are intended to be embraced therein.

The invention claimed is:

1. A method of providing cooling through the use of a garment, comprising:
   providing an inlet attached to the garment for connecting to a source of carbon dioxide ($CO_2$), and providing a series of conduits for directing the $CO_2$ about the garment;
   providing two-stage cooling by the garment wherein in a first stage the $CO_2$ is maintained in a liquid/gas biphasic state and in a second stage the $CO_2$ assumes a gaseous state; and
   providing a pressure regulator disposed between the first and second stages for maintaining the first stage in a generally liquid/gas biphasic state.

2. The method of claim 1 wherein in the first stage the method includes transferring heat from the wearer to the $CO_2$ by conduction and changing at least a portion of the $CO_2$ from a liquid state to a gaseous state, and wherein in the second stage the method includes transferring heat from the wearer by evaporative cooling and dispersing a gaseous $CO_2$ into an area adjacent the garment.

3. The method of claim 1 including directing $CO_2$ into the first stage such that a substantial portion of the $CO_2$ being directed into the first stage assumes a liquid state, and maintaining the pressure of the $CO_2$ in the first stage such that as the $CO_2$ moves through the first stage a substantial portion of the $CO_2$ changes from a liquid state to a gaseous state.

4. The method of claim 1 including connecting at least one manifold between the first and second stages.

5. The method of claim 1 including providing an expansion device upstream of the first stage for converting at least a portion of the $CO_2$ from a liquid phase to a gaseous phase.

6. A method of cooling a person by utilizing a garment worn by the person, the method comprising:
   directing a cooling medium into a liquid-gas cooling section formed in the garment;
   after directing the cooling medium into the liquid-gas cooling section, directing the cooling medium to an evaporative cooling section formed in the garment; and
   controlling the pressure of the cooling medium in the liquid-gas cooling section so as to maintain a liquid-gas state in the cooling section of the garment.

7. The method of claim 6 including controlling the pressure in the liquid-gas cooling section by utilizing a pressure regulator disposed between the liquid-gas cooling section and the evaporative cooling section to regulate the pressure within the liquid-gas cooling section.

8. The method of claim 6 including utilizing an expansion device disposed upstream from the liquid-gas cooling section and utilizing the expansion device to convert a portion of a cooling medium from a liquid state to a gaseous state.

9. The method of claim 6 wherein the liquid-gas cooling section includes a first set of conduits and wherein the evaporative cooling section includes a second set of conduits, and the method includes directing cooling medium to the first set of conduits and thereafter directing the cooling medium through the second set of conduits.

10. The method of claim 9 wherein the cooling medium is $CO_2$ and the method includes attaching a canister of $CO_2$ to the garment and maintaining the canister of $CO_2$ attached to the garment while the garment is being worn by a person and while the garment is cooling the person.

11. A method of cooling a living body or a part thereof with a garment worn by the living body, the method comprising:
   directing a cooling medium to the garment and directing the cooling medium about the garment;
   transferring heat from the living body to the cooling medium being directed about the garment; and
   in a first stage maintaining the cooling medium in a liquid/gas biphasic state and transferring heat from the living body or a portion thereof to the cooling medium and changing the cooling medium from a predominantly liquid phase to a predominantly gaseous phase.

12. The method of claim 11 wherein in a second stage the method includes maintaining the cooling medium in a substantially gaseous phase to further cool the living body wearing the garment.

13. The method of claim 11 including maintaining the pressure of the cooling medium in the first stage so as to enable the cooling medium to assume a generally liquid-gas biphasic state wherein as additional heat is transferred to the cooling medium, portions of the cooling medium in a liquid state are converted to a gaseous state.

14. The method of claim 12 including utilizing a pressure regulator disposed between the first and second stages to control the pressure of the cooling medium in the first stage.

15. The method of claim 11 wherein the cooling medium includes $CO_2$.

16. The method of claim 11 including providing an expansion device upstream of the first stage for converting at least a portion of the cooling medium from a liquid state to a gaseous state.

17. A method of cooling a living body comprising:
   directing a cooling medium to a garment worn by the body;
   distributing the cooling medium about one or more areas of the garment;
   changing the phase of the cooling medium from at least a partial liquid phase to a substantial gaseous phase in a first stage and maintaining the cooling medium in the first stage in a liquid/gas biphasic state; and
   directing the cooling medium from the first stage to a second stage where the cooling medium further cools the body.

18. The method of claim 17 including controlling the pressure of the cooling medium in the first stage such that the pressure of the cooling medium causes a substantial portion of the cooling medium to change from a liquid state to a gaseous state in the first stage.

19. The method of claim 18 including utilizing a pressure regulator downstream of the first stage for maintaining a selected pressure within the first stage and maintaining at least a portion of the cooling medium in a gaseous phase.

20. The method of claim 17 including in the second stage cooling the body by evaporative cooling by facilitating the body's natural cooling by evaporating perspiration from the body.

* * * * *